United States Patent
Tran et al.

(10) Patent No.: US 10,028,764 B2
(45) Date of Patent: Jul. 24, 2018

(54) ABLATION CATHETER WITH WIRELESS TEMPERATURE SENSOR

(71) Applicant: Boston Scientific Scimed, Inc., Maple Grove, MN (US)

(72) Inventors: Binh C. Tran, Minneapolis, MN (US); Brice Lee Shireman, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1036 days.

(21) Appl. No.: 14/186,116

(22) Filed: Feb. 21, 2014

(65) Prior Publication Data

US 2014/0236138 A1 Aug. 21, 2014

Related U.S. Application Data

(60) Provisional application No. 61/767,671, filed on Feb. 21, 2013.

(51) Int. Cl.
*A61B 18/12* (2006.01)
*A61B 17/32* (2006.01)
(Continued)

(52) U.S. Cl.
CPC .. *A61B 17/320068* (2013.01); *A61B 18/1492* (2013.01); *A61N 7/00* (2013.01);
(Continued)

(58) Field of Classification Search
CPC ........ A61B 17/320068; A61B 18/1492; A61B 2017/00101; A61B 2017/00221;
(Continued)

(56) References Cited

U.S. PATENT DOCUMENTS 5,154,387 A 10/1992 Trailer
5,275,162 A * 1/1994 Edwards ............... A61B 5/042
600/374
(Continued)

FOREIGN PATENT DOCUMENTS

EP 1690510 A1 8/2006
WO WO-2008118992 A1 10/2008
(Continued)

OTHER PUBLICATIONS

"U.S. Appl. No. 12/821,459, Non Final Office Action dated Aug. 20, 2012", 20 pgs.
(Continued)

*Primary Examiner* — Michael Peffley
*Assistant Examiner* — Amanda Zink

(57) ABSTRACT

Disclosed herein, among other things, are methods and apparatus related to ablation catheters with wireless temperature sensing. The present subject matter provides an ablation catheter system including an ablation transducer and a wireless temperature sensor. The wireless temperature sensor includes at least one temperature sensing element configured to sense a temperature-dependent parameter, circuitry configured to measure the sensed parameter and compute a temperature, a transmitter configured to wirelessly transmit a signal including at least one of the sensed parameter and the computed temperature, and a power supply. A controller is provided to coordinate timing of ablation therapy and sensing of the wireless temperature sensor, in various embodiments.

20 Claims, 8 Drawing Sheets

(51) Int. Cl.

| | |
|---|---|
| *A61N 7/00* | (2006.01) |
| *A61B 18/14* | (2006.01) |
| *A61B 18/00* | (2006.01) |
| *A61B 17/00* | (2006.01) |

(52) U.S. Cl.
CPC ............... *A61B 2017/00101* (2013.01); *A61B 2017/00221* (2013.01); *A61B 2018/00434* (2013.01); *A61B 2018/00511* (2013.01); *A61B 2018/00577* (2013.01); *A61B 2018/00791* (2013.01); *A61B 2018/00797* (2013.01)

(58) Field of Classification Search
CPC .......... A61B 2018/00434; A61B 2018/00511; A61B 2018/00577; A61B 2018/00791; A61B 2018/00797; A61N 7/00
See application file for complete search history.

(56) References Cited

U.S. PATENT DOCUMENTS

| | | | |
|---|---|---|---|
| 5,919,188 | A | 7/1999 | Shearon et al. |
| 6,053,912 | A | 4/2000 | Panescu et al. |
| 6,569,162 | B2 | 5/2003 | He |
| 6,602,242 | B1 | 8/2003 | Fung et al. |
| 6,640,120 | B1 | 10/2003 | Swanson et al. |
| 6,689,128 | B2 | 2/2004 | Sliwa, Jr. et al. |
| 6,804,545 | B2 | 10/2004 | Fuimaono et al. |
| 6,805,128 | B1 | 10/2004 | Pless et al. |
| 7,278,993 | B2 | 10/2007 | Kelly et al. |
| 7,387,126 | B2 | 6/2008 | Cox et al. |
| 8,221,409 | B2 | 7/2012 | Cao et al. |
| 9,192,790 | B2 * | 11/2015 | Hastings ............... A61B 8/0891 |
| 9,326,751 | B2 * | 5/2016 | Hastings ............... A61B 8/0841 |
| 2002/0019627 | A1 * | 2/2002 | Maguire ............ A61B 18/1492 606/27 |
| 2002/0107511 | A1 | 8/2002 | Collins et al. |
| 2003/0004506 | A1 | 1/2003 | Messing |
| 2004/0092806 | A1 | 5/2004 | Sagon et al. |
| 2005/0070894 | A1 | 3/2005 | McClurken |
| 2007/0043397 | A1 | 2/2007 | Ocel et al. |
| 2008/0091193 | A1 | 4/2008 | Kauphusman et al. |
| 2008/0161797 | A1 | 7/2008 | Wang et al. |
| 2008/0243214 | A1 | 10/2008 | Koblish |
| 2008/0249507 | A1 * | 10/2008 | Hadani ............... A61B 1/00105 604/523 |
| 2008/0300454 | A1 | 12/2008 | Goto |
| 2009/0093810 | A1 | 4/2009 | Subramaniam et al. |
| 2009/0112199 | A1 * | 4/2009 | Zhang .................. A61B 18/24 606/15 |
| 2010/0331658 | A1 | 12/2010 | Kim et al. |
| 2011/0009857 | A1 | 1/2011 | Subramaniam et al. |
| 2011/0022041 | A1 | 1/2011 | Ingle et al. |
| 2011/0028826 | A1 | 2/2011 | Kim et al. |
| 2011/0224667 | A1 | 9/2011 | Koblish et al. |
| 2012/0059286 | A1 * | 3/2012 | Hastings ............... A61N 7/022 601/2 |

FOREIGN PATENT DOCUMENTS

| | | |
|---|---|---|
| WO | WO-2009048824 A1 | 4/2009 |
| WO | WO-2009048943 A1 | 4/2009 |
| WO | WO-2011008444 A1 | 1/2011 |
| WO | WO-2011008681 A1 | 1/2011 |
| WO | WO-2011115787 A1 | 9/2011 |

OTHER PUBLICATIONS

"U.S. Appl. No. 12/821,459, Notice of Allowance dated Dec. 10, 2012", 8 pgs.
"U.S. Appl. No. 12/821,459, Response filed Jun. 11, 2012 to Restriction Requirement dated May 10, 2012", 10 pgs.
"U.S. Appl. No. 12/821,459, Response filed Nov. 20, 2012 to Non Final Office Action dated Aug. 20, 2012", 14 pgs.
"U.S. Appl. No. 12/821,459, Restriction Requirement dated May 10, 2012", 8 pgs.
"U.S. Appl. No. 13/043,301, Preliminary Amendment filed Mar. 8, 2011", 3 pgs.
"International Application Serial No. PCT/US2010/039600, International Search Report dated Nov. 10, 2010", 5 pgs.
"International Application Serial No. PCT/US2010/039600, Invitation to Pay Additional Fee dated Aug. 30, 2010", 6 pgs.
"International Application Serial No. PCT/US2010/039600, Written Opinion dated Nov. 10, 2010", 8 pgs.
"International Application Serial No. PCT/US2010/041677, International Search Report dated Aug. 20, 2010", 4 pgs.
"International Application Serial No. PCT/US2010/041677, Written Opinion dated Aug. 20, 2010", 6 pgs.
"International Application Serial No. PCT/US2011/027591, International Preliminary Report on Patentability dated Sep. 27, 2012", 7 pages.
"International Application Serial No. PCT/US2011/027591, International Search Report dated Jun. 17, 2011", 4 pgs.
"International Application Serial No. PCT/US2011/027591, Written Opinion dated Jun. 17, 2011", 6 pgs.

\* cited by examiner

ABLATION CATHETER WITH WIRELESS TEMPERATURE SENSOR

CLAIM OF PRIORITY

This application claims the benefit of priority under 35 U.S.C. § 119(e) of U.S. Provisional Patent Application Ser. No. 61/767,671, filed on Feb. 21, 2013, which is herein incorporated by reference in its entirety.

CROSS REFERENCE TO RELATED APPLICATION

This application is related to commonly assigned, U.S. Patent Application Ser. No. 61/767,665, entitled "ABLATION CATHETER SYSTEM WITH WIRELESS RADIO FREQUENCY TEMPERATURE SENSOR", filed on Feb. 21, 2013, which is hereby incorporated by reference in its entirety.

TECHNICAL FIELD

This application relates generally to medical devices and, more particularly, to systems and methods related to ablation catheters.

BACKGROUND

Renal sympathetic nerve activity has been identified as a contributor to hypertension, as patients with hypertension exhibit increased sympathetic activity relating to the kidneys. Ablation of renal nerves is one way of treating hypertension. In radio frequency (RF) ablation, RF energy is directed from the ablation electrode through tissue to ablate the tissue and form a lesion. Systems using other forms of energy, such as ultrasound, are also available for performing ablation.

Ablation has also been used in other applications. For example, ablation is one way of treating cardiac arrhythmias and restoring normal rhythm. The sources of aberrant electrical conduction are located, and the tissue is ablated.

Renal denervation and other catheter based ablation applications would benefit from real-time, active monitoring of tissue temperatures in the vicinity of the treatment target. Traditional temperature monitoring techniques that include wires which extend through the length of the catheter to a sensor at the catheter tip can adversely impact catheter performance and can be impractical. For example, the need to include a wire for each sensor adds bulk, stiffness, or diameter to the catheter affecting its size maneuverability, and possibly safe use. Conversely, the number of temperature sensors or monitoring points available in a catheter may be limited in order to maintain catheter functional characteristics. Wireless temperature monitoring technology for ablation catheter systems is described herein to mitigate limitations of traditional wired temperature sensors.

SUMMARY

Disclosed herein, among other things, are methods and apparatus related to ablation catheters with wireless temperature sensing. The present subject matter provides an ablation catheter system including an ablation transducer and a wireless temperature sensor. The wireless temperature sensor includes at least one temperature sensing element configured to sense a temperature-dependent parameter, circuitry configured to measure the sensed parameter and compute a temperature, a transmitter configured to wirelessly transmit a signal including at least one of the sensed parameter and the computed temperature, and a power supply. A controller is provided to coordinate timing of ablation therapy and sensing of the wireless temperature sensor, in various embodiments.

One aspect of the present subject matter provides an ablation catheter system including an ablation catheter configured for insertion into a human body and an ablation transducer connected to the catheter and configured to deliver ablative therapy to a target site. A wireless temperature sensor includes at least one temperature sensing element is configured to sense a temperature-dependent parameter and circuitry configured to measure the sensed parameter and compute the sensed temperature. Wireless transmission is provided by a communication module coupled to the catheter including a transmitter. The communication module is configured for wirelessly a signal including at least one of the sensed parameter and the computed temperature from the at least one temperature sensing element to an external device. In various embodiments, a power supply is configured to supply power to the ablation transducer and the wireless temperature sensor. A controller is configured to control timing of ablative therapy delivery, temperature measurement, and wireless data transmission, in various embodiments.

Another aspect of the present subject matter includes a method of using an ablation catheter with wireless temperature sensing. The method includes delivering electrical power through the ablation catheter from an electrical power supply and providing ablation therapy to a target site using an ablation transducer coupled to the ablation catheter. A temperature is sensed at or near the target site using at least one temperature sensing element coupled to the ablation catheter. A transmitter connected to the temperature sensing element transmits a signal including data to identify the temperature sensing element and the sensed temperature.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an," "one," or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Disclosed herein, among other things, are methods and apparatus related to ablation catheters with wireless temperature sensing. The present subject matter provides an ablation catheter system including an ablation transducer and a wireless temperature sensor. The wireless temperature sensor includes at least one temperature sensing element configured to sense a temperature-dependent parameter, circuitry configured to measure the sensed parameter and compute a temperature, a transmitter configured to wirelessly transmit a signal including at least one of the sensed parameter and the computed temperature, and a power supply. A controller is provided to coordinate timing of ablation therapy and sensing of the wireless temperature sensor, in various embodiments.

Some embodiments ablate renal nerves for the treatment of hypertension. Other types of tissue heating and ablation can be performed using the present systems and methods, without departing from the scope of the present subject matter. Hypertension is a chronic medical condition in which the blood pressure is elevated. Persistent hypertension is a significant risk factor associated with a variety of adverse medical conditions, including heart attacks, heart failure, arterial aneurysms, and strokes. Persistent hypertension is a leading cause of chronic renal failure. Hyperactivity of the sympathetic nervous system serving the kidneys is associated with hypertension and its progression. Renal denervation may reduce blood pressure by deactivating these sympathetic nerves, and may be a viable treatment option for many patients with hypertension who do not respond to conventional drugs.

Figure 1:
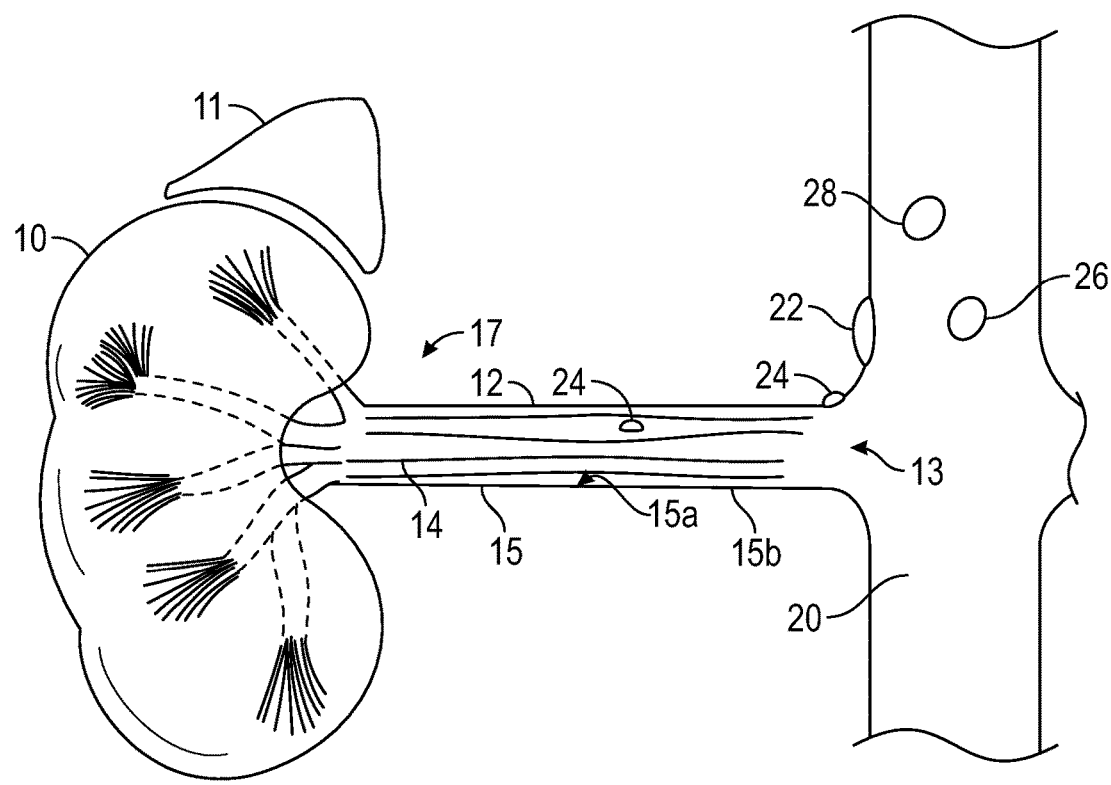
FIG. 1 is an illustration of a kidney and selected renal nerves and vasculature.

FIG. 1 is an illustration of a kidney 10 and renal vasculature including a renal artery 12 branching laterally from the abdominal aorta 20. The right and left kidneys are supplied with blood from the right and left renal arteries that branch from respective right and left lateral surfaces of the abdominal aorta 20. The right and left renal arteries extend from the abdominal aorta 20 to respective renal sinuses proximate the hilum 17 of the kidneys, and branch into segmental arteries and then interlobular arteries within the kidney 10. Also shown in FIG. 1 is the suprarenal gland 11, commonly referred to as the adrenal gland.

The autonomic nervous system of the body controls involuntary actions of the smooth muscles in blood vessels, the digestive system, heart, and glands. The autonomic nervous system includes the sympathetic nervous system and the parasympathetic nervous system. In general terms, the parasympathetic nervous system prepares the body for rest by lowering heart rate, lowering blood pressure, and stimulating digestion. The sympathetic nervous system effectuates the body's fight-or-flight response by increasing heart rate, increasing blood pressure, and increasing metabolism.

Figure 2A:
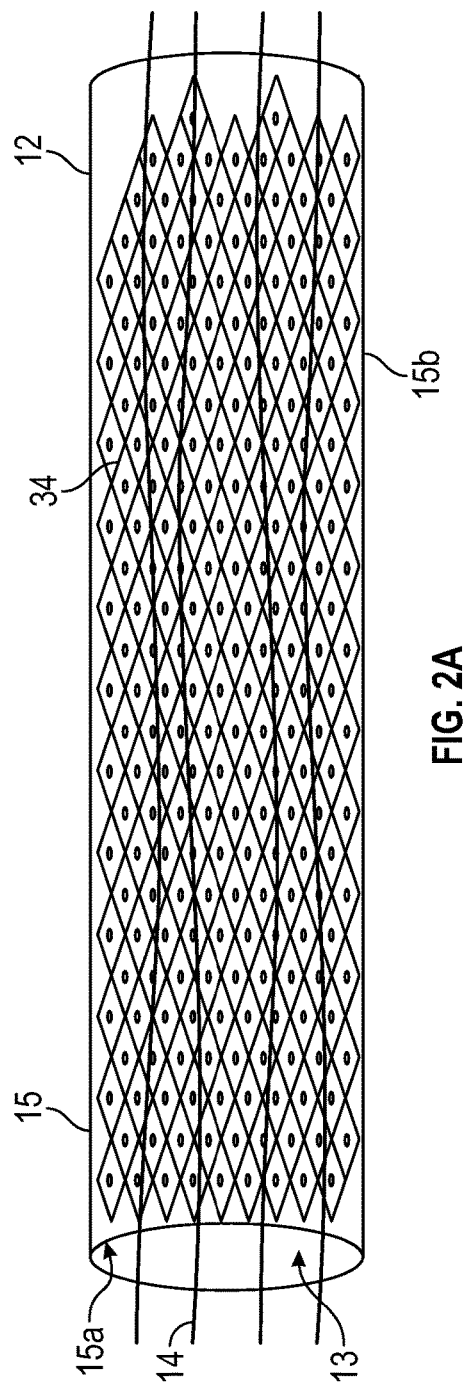
FIGS. 2A-2B illustrate innervation associated with the renal artery.
Figure 2B:
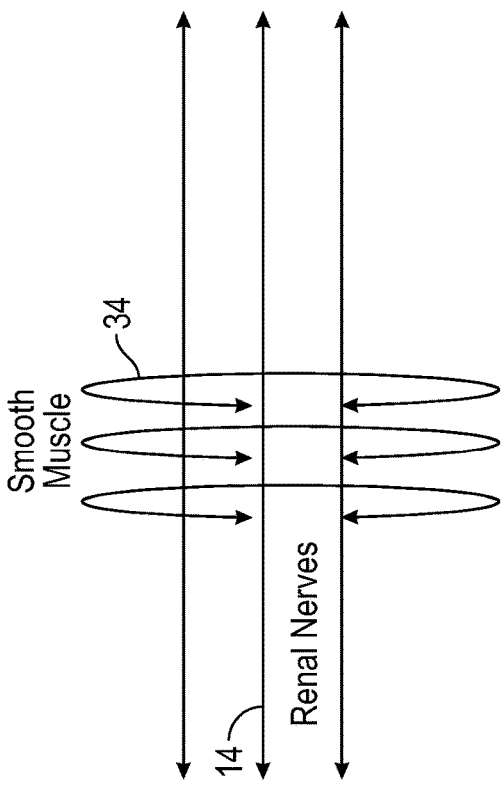

FIGS. 1 and 2A-2B illustrate sympathetic innervation associated with the renal vasculature, primarily innervation of the renal artery 12. Renal nerves 14 innervate the kidneys and ureters. The primary functions of sympathetic nerves associated with the renal vasculature include signaling to and from the kidney, regulation of renal blood flow and pressure, stimulation of renin release, and direct stimulation of water and sodium ion reabsorption.

Most of the nerves innervating the renal vasculature are sympathetic fibers arising from the superior mesenteric ganglion 26. The renal nerves 14 extend generally axially along the renal arteries 12, enter the kidneys 10 at the hilum 17, follow the branches of the renal arteries 12 within the kidney 10, and extend to individual nephrons. Nerve fibers from other renal ganglia, such as the renal ganglia 24, the left and right aorticorenal ganglia 22, and celiac ganglia 28 also innervate the renal vasculature. The celiac ganglion 28 is joined by the greater thoracic splanchnic nerve (greater TSN). The aorticorenal ganglia 26 is joined by the lesser thoracic splanchnic nerve (lesser TSN) and innervates the greater part of the renal plexus.

Sympathetic signals to the kidney 10 are communicated via innervated renal vasculature that originates primarily at spinal segments T10-T12 and L1. Parasympathetic signals originate primarily at spinal segments S2-S4 and from the medulla oblongata of the lower brain. Sympathetic nerve traffic travels through the sympathetic trunk ganglia, where some may synapse, while others synapse at the aorticorenal ganglion 22 (via the lesser thoracic splanchnic nerve, i.e., lesser TSN) and the renal ganglion 24 (via the least thoracic splanchnic nerve, i.e., least TSN). The postsynaptic sympathetic signals then travel along nerves 14 of the renal artery 12 to the kidney 10. Presynaptic parasympathetic signals travel to sites near the kidney 10 before they synapse on or near the kidney 10.

The renal artery 12 is lined with smooth muscle 34 that controls the diameter of the renal artery lumen 13. The renal nerves 14 innervate the smooth muscle 34 of the renal artery wall 15 and extend lengthwise in a generally axial or longitudinal manner along the renal artery wall 15. The smooth muscle 34 surrounds the renal artery circumferentially, and extends lengthwise in a direction generally transverse to the longitudinal orientation of the renal nerves 14. The smooth muscle 34 of the renal artery 12 is under involuntary control of the autonomic nervous system. An increase in sympathetic activity, for example, tends to contract the smooth muscle 34, which reduces the diameter of the renal artery lumen 13 and decreases blood perfusion. A decrease in sympathetic activity tends to cause the smooth muscle 34 to relax, resulting in vessel dilation and an increase in the renal artery lumen diameter and blood perfusion. Conversely, increased parasympathetic activity tends to relax the smooth muscle 34, while decreased parasympathetic activity tends to cause smooth muscle contraction.

Figure 3A:
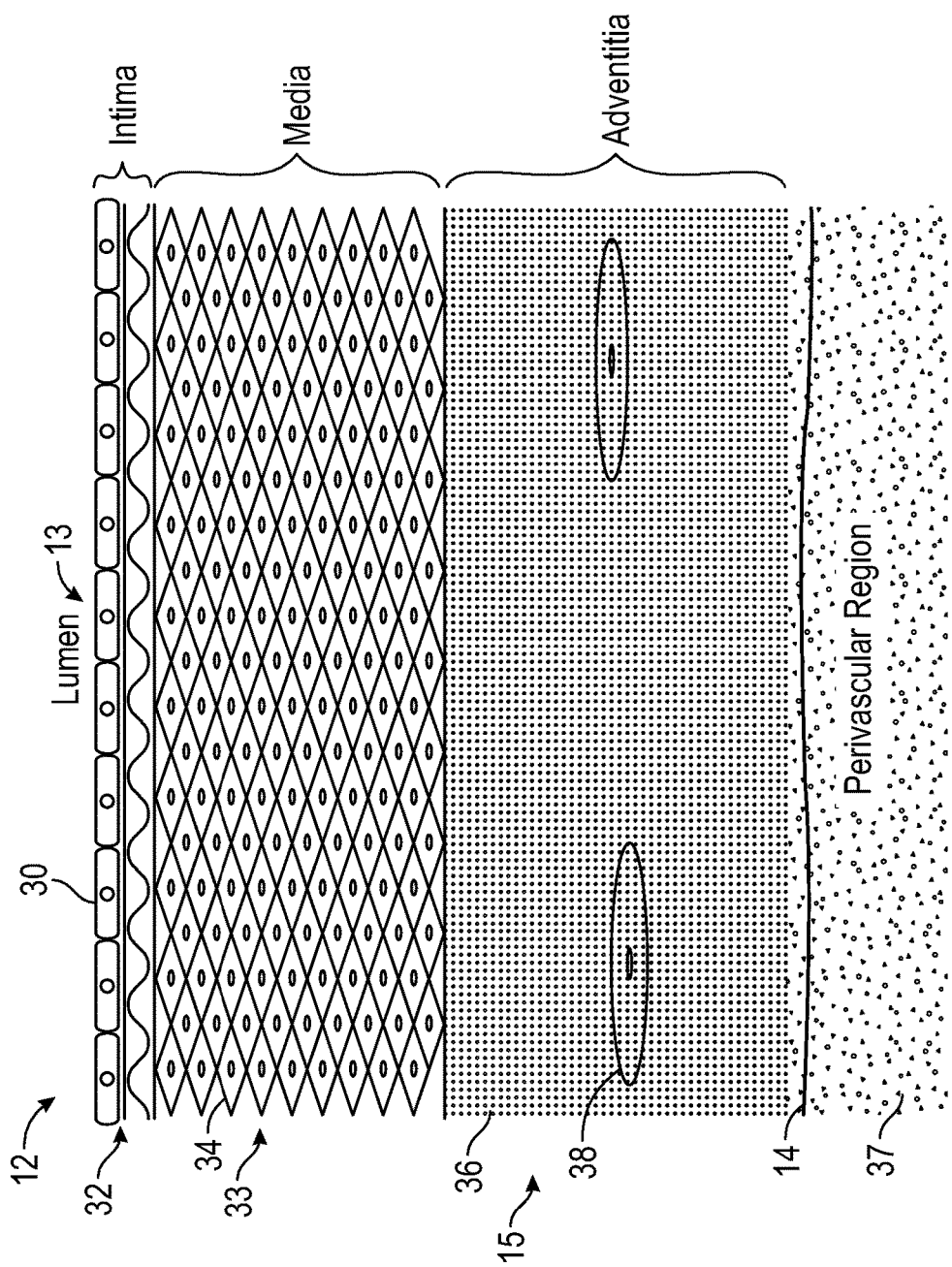
FIGS. 3A-3C illustrate various portions of the renal nerve and artery.

FIG. 3A shows a segment of a longitudinal cross-section through a renal artery, and illustrates various tissue layers of the wall 15 of the renal artery 12. The innermost layer of the renal artery wall 15 is the intima, which is lined with endothelium 30, which is supported by an internal elastic lamina 32. The endothelium 30 is a single layer of cells that contacts the blood flowing though the vessel lumen 13. Endothelium cells are typically polygonal, oval, or fusiform, and have very distinct round or oval nuclei. Cells of the endothelium 30 are involved in several vascular functions, including control of blood pressure by way of vasoconstriction and vasodilation, blood clotting, and acting as a barrier layer between contents within the lumen 13 and surrounding tissue, including the inner elastic lamina 32.

Adjacent the intima is the media 33, which is the middle layer of the renal artery wall 15. The media is made up of smooth muscle 34 and elastic tissue. The media 33 can be readily identified by its color and by the transverse arrangement of its fibers. More particularly, the media 33 consists principally of bundles of smooth muscle fibers 34 arranged in a thin plate-like manner or lamellae and disposed circularly around the arterial wall 15. The outermost layer of the renal artery wall 15 is the adventitia 36, which is largely made up of connective tissue. The adventitia 36 includes fibroblast cells 38 that play an important role in wound healing.

Figure 3B:
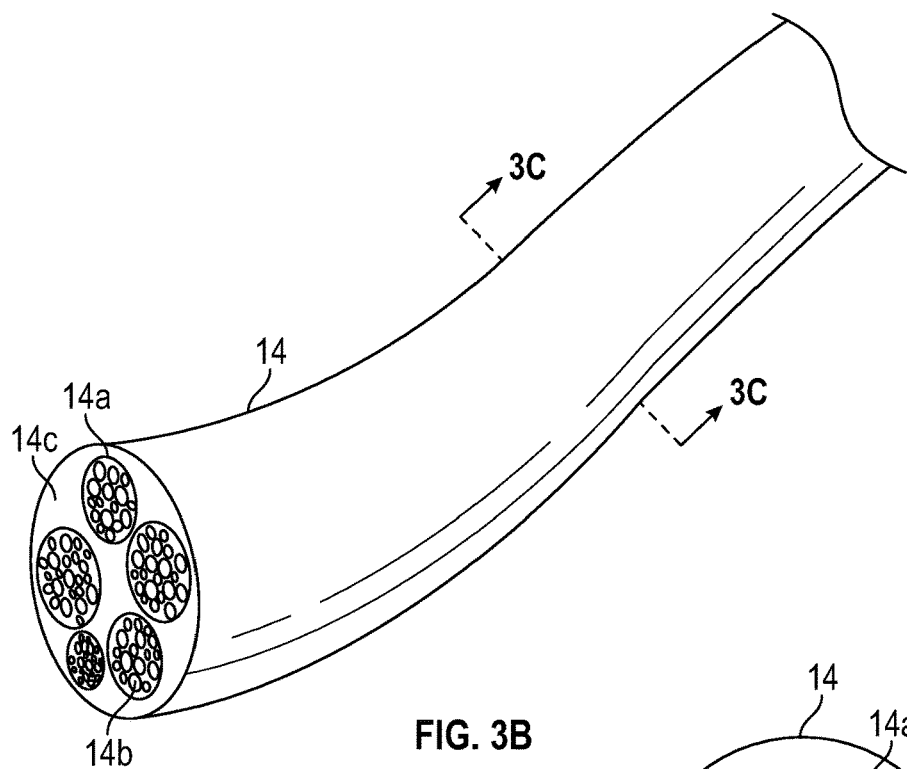
Figure 3C:
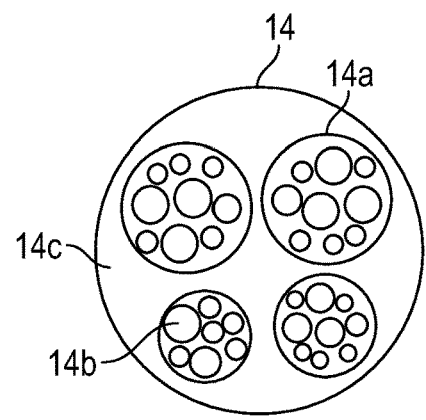

A perivascular region 37 is shown adjacent and peripheral to the adventitia 36 of the renal artery wall 15. A renal nerve 14 is shown proximate the adventitia 36 and passing through a portion of the perivascular region 37. The renal nerve 14 is shown extending substantially longitudinally along the outer wall 15 of the renal artery 12. The main trunk of the renal nerves 14 generally lies in or on the adventitia 36 of the renal artery 12, often passing through the perivascular region 37, with certain branches coursing into the media 33 to innervate the renal artery smooth muscle 34. FIGS. 3B and 3C illustrate the renal nerve 14 in more detail. Bundles 14a of nerve fibers 14b each comprise axons or dendrites that originate or terminate on cell bodies or neurons located in ganglia or on the spinal cord, or in the brain. Supporting tissue structures 14c of the nerve 14 include the endoneurium (surrounding nerve axon fibers), perineurium (surrounds fiber groups to form a fascicle), and epineurium (binds fascicles into nerves), which serve to separate and support nerve fibers 14b and bundles 14a.

In some embodiments, a treatment apparatus of the disclosure may be implemented to deliver denervation therapy that causes transient and reversible injury to renal nerve fibers 14b. In other embodiments, a treatment apparatus of the disclosure may be implemented to deliver denervation therapy that causes more severe injury to renal nerve fibers 14b, which may be reversible if the therapy is terminated in a timely manner. In still other embodiments, a treatment apparatus of the disclosure may be implemented to deliver denervation therapy that causes even more severe injury to renal fibers 14b, which may be irreversible.

Figure 4:
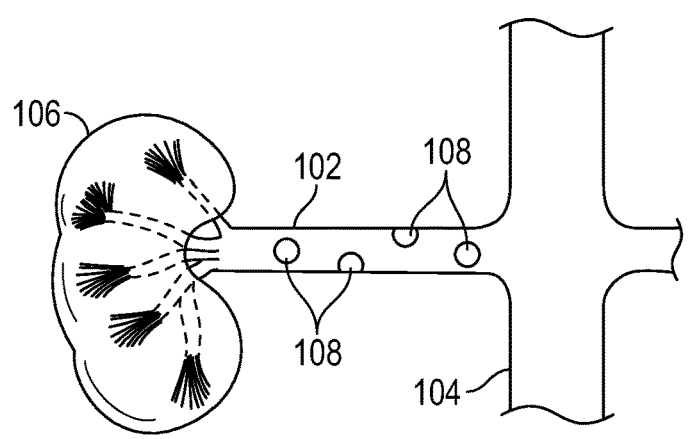
FIG. 4 illustrates ablation sites along the renal artery.

FIG. 4 illustrates ablation sites 108 along the renal artery 102, which connects a kidney 106 to the aorta 104. Ablation of perivascular renal nerves has been used as a treatment for hypertension. RF or ultrasonic (acoustic) energy can be used for renal denervation for treatment of hypertension, in various embodiments. For example, RF or ultrasonic energy can be delivered from a catheter situated in the renal artery to tissues containing a renal nerve, just beyond the vessel wall. Therapy effectiveness may be affected by differences in local anatomy from patient to patient. RF electrodes on catheters placed in the renal artery can be used to ablate the nerves, but with risk of artery wall injury. To control injury to the artery wall, one method is to move the RF electrode to ablate at discrete locations along and around the artery; this can cause local renal artery injury due to the local high temperatures resulting from high current density near the electrodes, but reduces the potential for significant stenotic narrowing of the artery after the ablation procedure. In some approaches, a spiral pattern of ablation spots has been used to ablate the nerves while minimizing injury to the vessel wall. However, reliably positioning the electrode to ensure the desired relative spacing between ablation spots has been difficult, and repeated ablation cycles is also time-consuming. In some cases, it is desirable to independently monitor temperature at each ablation site, to distribute the ablation energy as desired and prevent injury to tissue. Real time temperature monitoring can provide instantaneous feedback useful for adjusting therapy parameters such as power and duration, to ensure treatment effectiveness. However, multipoint temperature monitoring using wired temperature sensors has been impractical due to the increased bulk and stiffness added to the catheter by the separate electrical wires attached to each temperature sensor. An improved system capable of concurrent temperature monitoring and ablation therapy is needed.

Various devices, including thermocouples, thermistors, and resistance temperature detectors (RTD) are capable of sensing temperature changes at the distal renal ablation site. In these devices an electrical parameter—typically voltage or resistance—changes in relation to a temperature change. A circuit is configured to measure the change in the parameter to derive the temperature change or temperature. Wires are used to connect to the device to the electrical circuit and transfer the data to a digital display. For an intravascular catheter the wires need to be reduced or eliminated in order to minimize the impact on the catheter performance. One way to reduce the number of wires running along or within the lumen of the catheter is to wirelessly transmit the temperature data to an external device.

Figure 6:
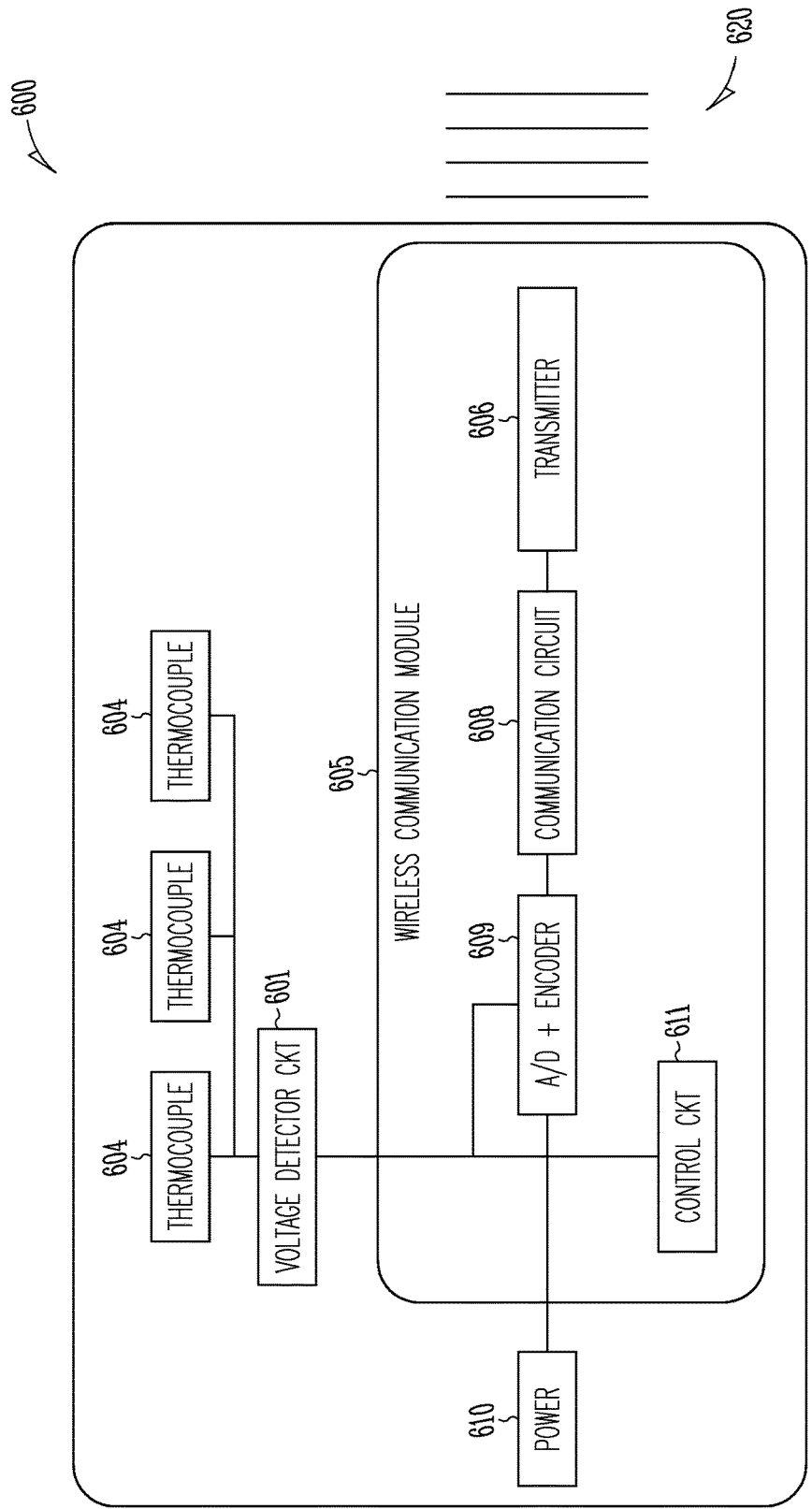
FIG. 6 illustrates a block diagram of wireless temperature sensor for an ablation catheter system with wireless temperature sensing, according to various embodiments of the present subject matter.

FIG. 6 illustrates a block diagram of wireless temperature sensor for an ablation catheter system with wireless temperature sensing, according to various embodiments of the present subject matter. The wireless temperature sensor 600 includes one or more temperature sensing elements 604. The depicted embodiment employs thermocouples as temperature sensing elements 604. The temperature sensing elements 604 are connected by short and fine electrical conductors to an electrical detector circuit 601, such as a voltage detector circuit, disposed within close proximity to the temperature sensing elements. A communication module 605 is connected to the detector circuit 601 to determine and transmit temperature information. In various embodiments, the communication module 605 includes a transmitter 606, communication circuitry 608, a controller 611, and a multichannel analog-to-digital (A/D) converter 609. In various embodiments, a power supply 610 is configured to supply power to the temperature sensor 600, including the transmitter 606. The communication module 605 is configured to transmit a wireless signal 620 including temperature data from the at least one temperature sensing element 604 to an external device (not depicted), in various embodiments.

In one embodiment, continuous temperature monitoring is performed simultaneously with continuous ablation therapy. In yet other embodiments, temperature measurement is interspersed with ablation therapy. In some embodiments, acoustic waves are utilized as the mode of wireless communication, minimizing the possibility of interference between the communication signal and the ablation therapy and enabling simultaneous monitoring and therapy. As depicted, acoustic, specifically ultrasonic signals in the frequency range in the tens of kHz range to tens of MHz are used. Yet other types of wireless communication (such as RF, inductive, etc.) can be used without departing from the scope of the present subject matter. In other embodiments, radio frequency (RF) waves are the mode of wireless communication, thus the communication module 605 and transmitter 606 are configured to operate with a RF wireless signal 620. In some embodiments, RF signals in the Industrial, Scientific and Medical (ISM), Medical Implant Communication Service (MICS), or Short Range Device (SRD) radio bands may be used. The frequency range of these signals ranges from 400 MHz to 950 MHz According to various embodiments, a unique identification code for each temperature sensing element is transmitted along with the temperature data to allow the external reader to distinguish which site the temperature data was measured from. With temperature monitoring of each ablation site available wirelessly, this information can be used as a feedback control to regulate the ablation energy delivered in a closed loop system.

Various embodiments of the present subject matter include a temperature reader (external device) outside the body, and a temperature sensor with multiple temperature sensing elements inside the body positioned at each appropriate treatment site in the renal arteries. In an embodiment, the external device is capable of receiving signals for each temperature sensing element, and each signal is encoded with the sensing element's identification and temperature data. In various embodiments, a portion of the external device including a receiver to receive the wireless signal is configured to rest upon the patient's body, such as in the form of a wand or pad. In various embodiments, the external device can be reused for multiple procedures. The external device can be powered using a standard AC plug or powered via internal batteries, in various embodiments.

Figure 5A:
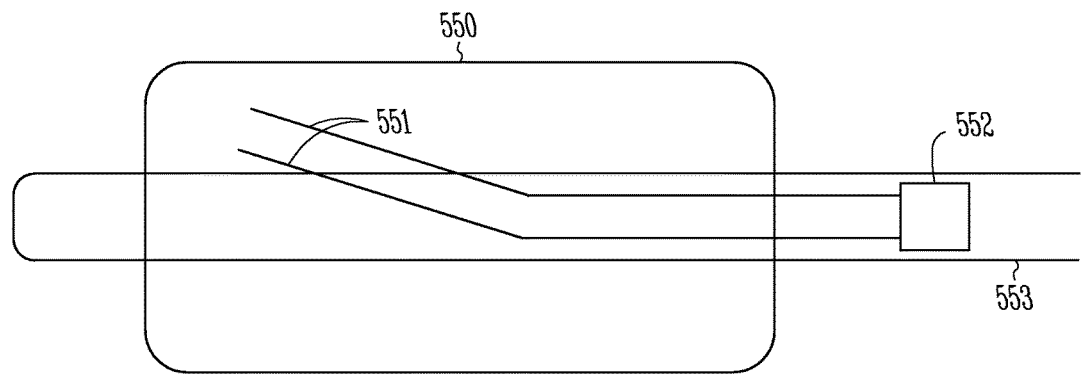
FIGS. 5A-5B illustrate ablation catheter systems with wireless temperature sensing, according to various embodiments of the present subject matter.

In various embodiments, renal ablation devices use a balloon to center and stabilize the catheter within the lumen of the vessel. In other embodiments, a balloon is configured as an integral component to deliver the RF energy to each site in the renal arteries. FIG. 5A illustrates how temperature sensing elements are integrated onto the surface of ablation catheters equipped with a balloon, in an embodiment. The balloon 550 contacting the vessel wall has at least one wireless temperature sensing element disposed within the balloon to sense temperature in the proximity of the vessel wall. In various embodiments, thin wires 551 made of differing metal types are patterned onto the surface of the balloon to form a temperature sensing element (such as thermocouple 604 in FIG. 6). The wires extend along the surface of the balloon and connect to a circuit assembly 552 integrated into the catheter body 553, the circuit assembly 552 including such elements as the electrical detector circuit 601 and communication module 605 with transmitter 606, communication circuitry 608, a controller 611 shown in FIG. 6. In some embodiments, the power supply 610 is comprised of a battery (not depicted) disposed within the catheter body. In another embodiment, power is supplied by an external power source (not depicted) via one or more power lines within or along the catheter shaft. In yet another embodiment the one or more power lines may serve as a single channel for transmitting temperature data from the temperature sensor to the external device.

Figure 5B:
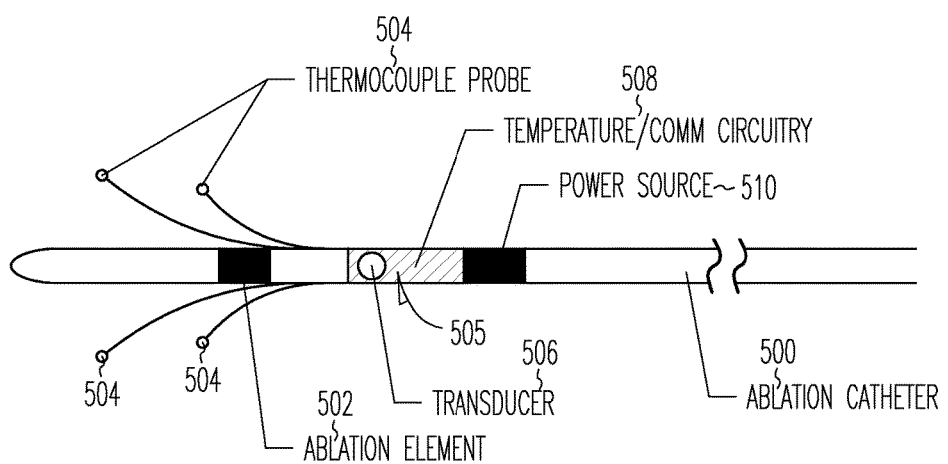

FIG. 5B illustrates an ablation catheter system with wireless temperature sensing, according to various embodiments of the present subject matter. The system 500 enables real time temperature monitoring during therapy and includes an ablation catheter 500 configured for insertion into a human body and an ablation transducer 502 connected to the catheter and configured to deliver ablative therapy to a target site. At least one temperature sensing element 504 is configured to sense a temperature at the target site. According to various embodiments, the ablation catheter includes flared memory-shaped wires configured to deploy the wireless temperature sensor at or near a vessel wall. A communication module 505 coupled to the catheter includes a transducer 506 and communication circuitry 508. The communication module 505 is configured for wirelessly transmitting temperature data from the at least one temperature sensing element 504 to an external device. In various embodiments, a power supply 510 is configured to supply power to the ablation transducer and the acoustic communication module.

According to various embodiments, the temperature sensing element is a short (small) thermocouple incorporated into a small diameter catheter. In one embodiment, the thermocouple is a type E thermocouple made from Chromel and Constantan to provide increased temperature sensitivity (i.e., the largest change in voltage for each change in degree of temperature). In various embodiments, the present subject matter includes multiple sensing elements for each device positioned at each ablation site. While a thermocouple sensing element has been discussed, alternate types of temperature sensing elements, such as a resistance temperature detector (RTD) or thermistor can be used without departing from the scope of the present subject matter. In addition, while the present discussion includes ablation catheters, the wireless temperature sensing discussed herein can be any medical device that either senses or controls the heating and cooling of the device and/or treatment site.

One embodiment of the present subject matter includes an ablation system with temperature sensing and wireless acoustic telemetry. The system includes a catheter for delivering ablative therapy, the catheter including: an ablation transducer; one or more temperature sensing elements connected to an electronic circuit; an acoustic transducer and communication module for transmitting temperature data; one or more energy sources for powering the ablation transducer and the acoustic communication module; a master control circuit to control the timing of therapy and measurement; and an external receiver with power source for receiving the acoustic communication signals and decoding the temperature data. In various embodiments, the catheter delivers RF or ultrasonic energy for performing ablation. The catheter includes multiple temperature sensing elements, such as thermocouples, connected to multichannel electronics, to perform multipoint temperature sensing, in various embodiments. The acoustic communications protocol includes encoding to identify which thermocouple each temperature measurement is associated with, according to various embodiments. In various embodiments, the system contains a master controller to synchronize therapy delivery, temperature measurement, and acoustic transmit and receive functions.

Figure 7:
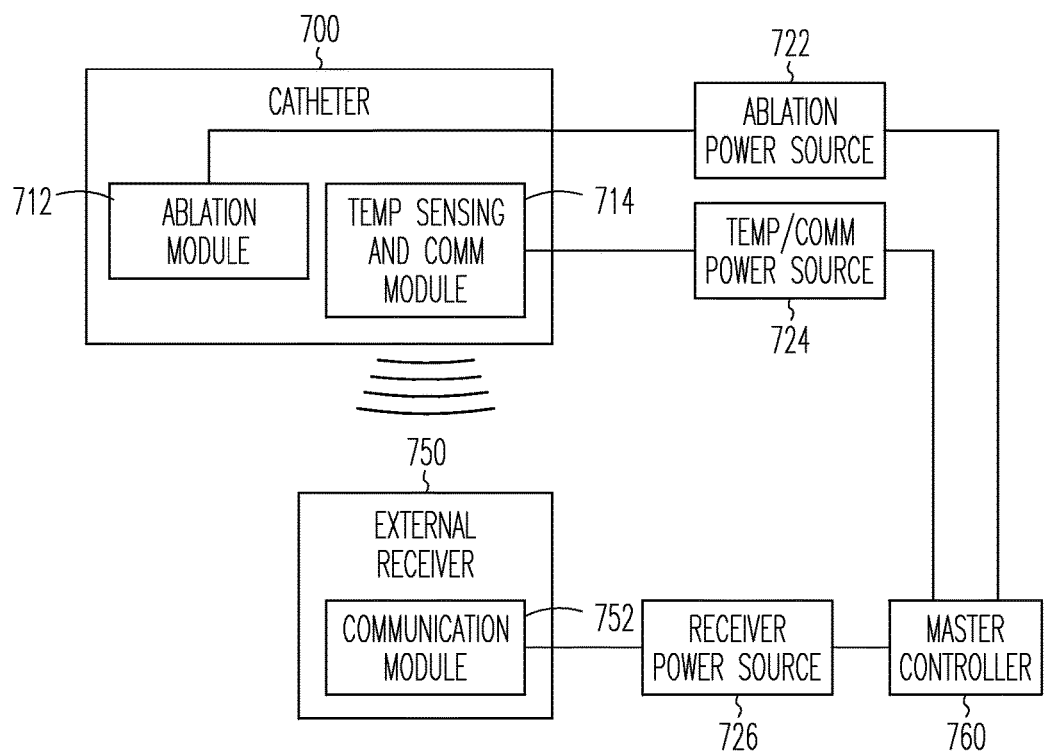
FIG. 7 illustrates an ablation catheter system with wireless temperature sensing and an external device, according to various embodiments of the present subject matter.

FIG. 7 illustrates an ablation catheter system with wireless temperature sensing and an external device, according to various embodiments of the present subject matter. The catheter 700 includes an ablation module 712 for therapy delivery and a temperature sensing and communication module 714 for sensing temperature and wireless transmitting temperature and identification data to an external device 750. The external device 750 includes a communication module 752 for communicating with the catheter, in various embodiments. In the depicted embodiment, separate power supplies 722, 724, 726 are used to provide electrical power for ablation, for temperature sensing and communication for the external device. In various embodiments, one or more of these can share a power supply. A master controller 760 is provided to synchronize therapy delivery, temperature measurement, and wireless transmit and receive functions for the catheter and external device. In one embodiment, the master controller is included in the external device. In various embodiments, one or more of the power supplies are included with the catheter. One or more of the power supplies are included in the external device, according to various embodiments. In various embodiments, the external device can be reused for multiple procedures. The external device can be powered using a standard AC plug or powered via internal batteries, in various embodiments. In an embodiment, the external device is capable of receiving ultrasound signals from each temperature sensor, and each signal is encoded with the sensor's identification and temperature data.

Figure 8:
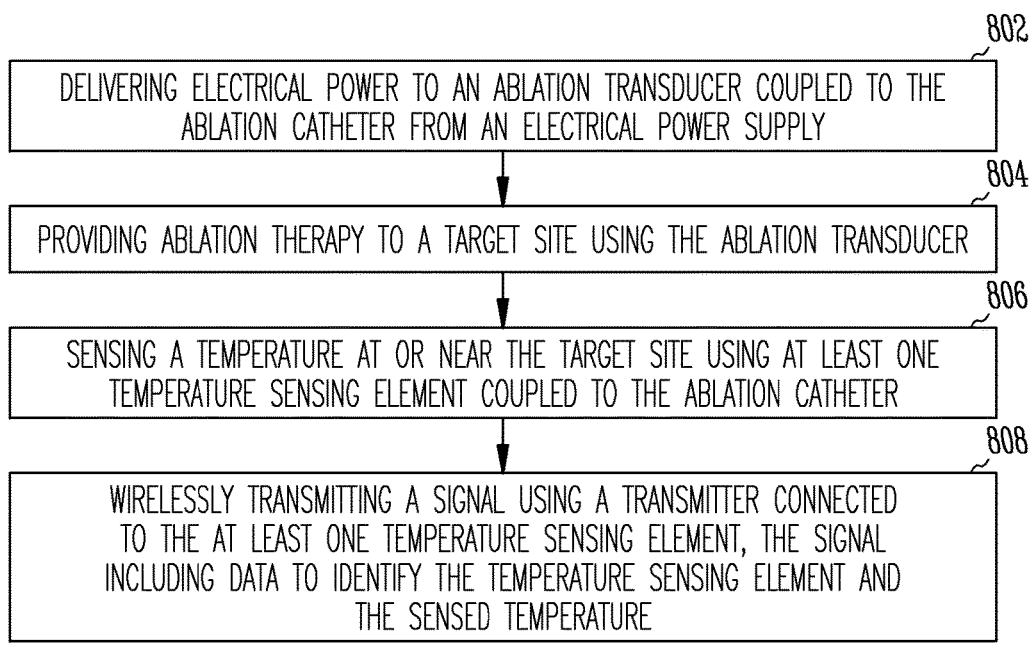
FIG. 8 illustrates a flow diagram of a method of using an ablation catheter with wireless temperature sensing, according to various embodiments of the present subject matter.

FIG. 8 illustrates a flow diagram of a method of using an ablation catheter with wireless temperature sensing, according to various embodiments of the present subject matter. The method includes delivering electrical power to the ablation catheter from an electrical power supply, at 802, and providing ablation therapy to a target site using an ablation transducer coupled to the ablation catheter, at 804. At 806, a temperature is sensed at the target site using a temperature sensing element coupled to the ablation catheter. A signal is wirelessly transmitted using a transmitter connected to the temperature sensing element, the signal including data to identify the temperature sensing element and the sensed temperature, at 808. In various embodiments, the ablation catheter delivers RF energy to induce tissue damage, for an application such as renal denervation. The ablation catheter delivers ultrasound or acoustic energy to induce tissue damage, in various embodiments.

In various embodiments, the ablation catheter with wireless temperature sensor is single use disposable. The external device for receiving and decoding the temperature signal is reusable, in various embodiments.

One of ordinary skill in the art will understand that, the modules and other circuitry shown and described herein can be implemented using software, hardware, and/or firmware. Various disclosed methods may be implemented as a set of instructions contained on a computer-accessible medium capable of directing a processor to perform the respective method.

This application is intended to cover adaptations or variations of the present subject matter. It is to be understood that the above description is intended to be illustrative, and not restrictive. For example, the present subject matter can be applied to other medical procedures where heating or ablation of tissue is desired. The scope of the present subject matter should be determined with reference to the appended claims, along with the full scope of legal equivalents to which such claims are entitled.

What is claimed is:

1. An ablation catheter system, comprising:
    an ablation catheter; and
    a wireless temperature sensor disposed at a distal end of the ablation catheter, the wireless temperature sensor including:
        at least one temperature sensing element configured to sense a temperature-dependent parameter;
        circuitry configured to measure the sensed parameter and compute a temperature;
        a transmitter configured to wirelessly transmit a signal including at least one of the sensed parameter and the computed temperature; and
        a power supply.

2. The system of claim 1, wherein the temperature sensing element is disposed on a balloon attached to the catheter, the balloon in contact with an inner surface of a biological lumen or chamber.

3. The system of claim 1, wherein the temperature sensing element is disposed on a flared memory-shaped wire configured to deploy in contact with an inner surface of a biological lumen or chamber.

4. The system of claim 1, wherein the temperature sensing element includes a thermocouple, thermistor, or resistance temperature detector (RTD).

5. The system of claim 1, wherein the transmitter includes a radio frequency (RF) transmitter.

6. The system of claim 1, wherein the transmitter includes an acoustic transducer.

7. The system of claim 1, wherein the transmitter is configured to transmit encoded data to identify the at least one temperature sensing element.

8. The system of claim 1, wherein the power supply is a battery disposed upon the catheter.

9. An ablation catheter system, comprising:
    an ablation catheter configured for insertion into a human body;
    an ablation transducer connected to the catheter and configured to deliver ablative therapy to a target site;
    a wireless temperature sensor disposed at a distal end of the ablation catheter and configured to sense a temperature at the target site, the wireless temperature sensor including:
        at least one temperature sensing element configured to sense a temperature-dependent parameter;
        circuitry configured to measure the sensed parameter and compute the sensed temperature; and
        a communication module including a transmitter, the communication module configured for wirelessly transmitting a signal including at least one of the sensed parameter and the computed temperature to an external device;
    at least one power supply configured to supply power to the ablation transducer and the wireless temperature sensor; and
    a controller connected to the at least one power supply and configured to control timing of ablative therapy delivery, temperature measurement, and wireless data transmission.

10. The system of claim 9, further comprising a balloon connected to the ablation catheter, wherein the temperature sensing element is connected to the balloon.

11. The system of claim 9, further comprising flared memory-shaped wires connected to the ablation catheter, wherein the temperature sensing element is connected to at least one of the memory-shaped wires.

12. The system of claim 9, wherein the controller is configured to regulate the ablative therapy using the temperature data in a closed loop system.

13. The system of claim 9, wherein the external device is configured to receive and decode the signal to identify the temperature and the temperature sensing element that sensed the temperature.

14. The system of claim 9, wherein the communication module is configured to transmit an acoustic signal having a frequency of approximately 20 kHz to 20 MHz.

15. The system of claim 9, wherein the communication module is configured to transmit a radio frequency signal having a frequency of approximately 400 MHz to 950 MHz.

16. The system of claim 9, wherein the ablation transducer is configured to deliver radio frequency (RF) energy for ablative therapy.

17. The system of claim 9, wherein the at least one power supply comprises a first power supply configured to supply power to the ablation transducer and a second power supply configured to supply power to the wireless temperature sensor, and wherein the second power supply is disposed at the distal end of the ablation catheter.

18. A method of using the ablation catheter system of claim 10, the method comprising:
- inserting the ablation catheter into a human body;
- delivering electrical power to the ablation transducer from the at least one power supply;
- providing ablation therapy to a target site using the ablation transducer;
- sensing a temperature at or near the target site using the wireless temperature sensor; and
- wirelessly transmitting a signal using the transmitter, the signal including data to identify at least one of the sensed parameter and the computed temperature.

19. The method of claim 18, further comprising controlling ablation therapy using the sensed temperature.

20. The method of claim 18, wherein sensing the temperature includes sensing the temperature using a thermocouple, thermistor or RTD.

* * * * *